United States Patent [19]

Skuballa et al.

[11] Patent Number: 4,721,729
[45] Date of Patent: Jan. 26, 1988

[54] NOVEL CARBACYCLINS, PROCESS FOR THE PREPARATION THEREOF, AND THEIR USE AS MEDICINAL AGENTS

[75] Inventors: Werner Skuballa; Bernd Raduechel; Helmut Vorbrueggen; Robert Nickolson; Martin Haberey; Olaf Loge; Claus-Steffen Stuerzebecher, all of Berlin, Fed. Rep. of Germany

[73] Assignee: Schering Aktiengesellschaft, Berlin and Bergkamen, Fed. Rep. of Germany

[21] Appl. No.: 702,092

[22] Filed: Feb. 8, 1985

[30] Foreign Application Priority Data

Feb. 10, 1984 [DE] Fed. Rep. of Germany ....... 3405181

[51] Int. Cl.$^4$ .................. C07C 177/00; A61K 31/557
[52] U.S. Cl. .................... 514/691; 514/729; 549/415; 568/374; 568/819
[58] Field of Search .............. 568/374, 819; 560/119; 562/501; 549/415; 514/691, 729

[56] References Cited

U.S. PATENT DOCUMENTS

| | | | | |
|---|---|---|---|---|
| 4,256,745 | 3/1981 | Skuballa | | 568/379 |
| 4,307,112 | 12/1981 | Gandolfi | | 514/277 |
| 4,497,830 | 2/1985 | Skuballa | | 514/277 |

*Primary Examiner*—Robert Gerstl
*Attorney, Agent, or Firm*—Millen & White

[57] ABSTRACT

Carbacyclins of Formula I

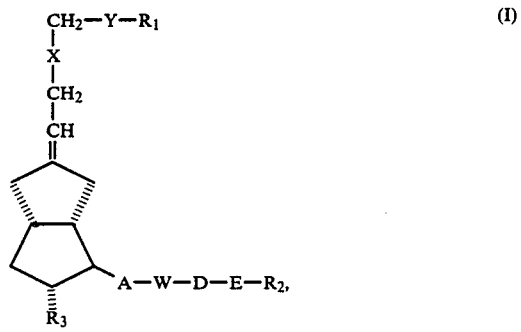

wherein
$R_1$ is an alkyl, cycloalkyl, aryl, aralkyl, or heterocyclic group,
Y is a keto group or a hydroxymethylene group,
X is a —$CH_2$— group or an oxygen atom,
A is a —$CH_2$—$CH_2$—, a trans—CH=CH— or a —C≡C— group,
W is a hydroxymethylene group or a

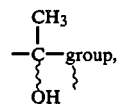

D is the group

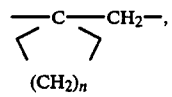

a straight-chain or branched, saturated alkylene group or unsaturated alkylene group of up to 5 carbon atoms which can optionally be substituted by 1-2 fluorine atoms,
n is 1, 2 or 3,
E is a direct bond, a —C≡C— group or a —$CR_4$=C-$R_5$— group wherein $R_4$ is hydrogen or an alkyl group and $R_5$ is hydrogen, halogen or an alkyl group,
$R_2$ is an alkyl, cycloalkyl, aryl, or heterocyclic group, and
$R_3$ is a hydroxy group,
are valuable, e.g., as cytoprotective agents.

16 Claims, No Drawings

NOVEL CARBACYCLINS, PROCESS FOR THE PREPARATION THEREOF, AND THEIR USE AS MEDICINAL AGENTS

BACKGROUND OF THE INVENTION

This invention relates to novel carbacyclin derivatives, a process for their preparation, as well as their use as medicinal agents.

The precursor of carbacyclins, prostacyclin, was isolated in 1976. Its structure was clarified in the same year (Postaglandins 12 : 915, 1976). For some time, as a prostaglandin abbreviation, the designation $PGI_2$ has become accepted for prostacyclin. Correspondingly, carbacyclins are also called 6a-carbaprostaglandins $I_2$.

The nomenclature of the compounds of this invention is based on a proposal by Morton and Brokaw (J. Org. Chem. 44 : 2280 [1979]). The synthesis of these compounds in all cases yields two double-bond isomers characterized by the symbols (5E) or (5Z).

Based on their biological and pharmacological properties, prostacyclins and their analogs are suitable for therapy and prophylaxis of thromboses, infarctions, and other cardiovascular diseases. The duration of activity of these compounds is frequently still too brief for therapeutic purposes. For this reason, all structural modifications of known $PGI_2$ derivatives pursue the objective of prolonging the period of efficacy, increasing the selectivity of activity, and simultaneously reducing the effective dose.

SUMMARY OF THE INVENTION

Accordingly, it is an object of this invention to provide prostacyclins having improved properties.

Upon further study of the specification and appended claims, further objects and advantages of this invention will become apparent to those skilled in the art.

It has now been found that, by replacing the 1-carboxy group in the 6a-carbaprostaglandin $I_2$ derivatives by a substituted keto group or a corresponding secondary alcohol group, it is possible to attain higher selectivity, improved efficacy and longer duration of activity. The resultant novel compounds possess the pharmacological properties typical of carbacyclins, but are particularly suited for cytoprotection in connection with the stomach, intestine, heart, kidneys, liver, and pancreas.

The invention concerns carbacyclins of Formula I

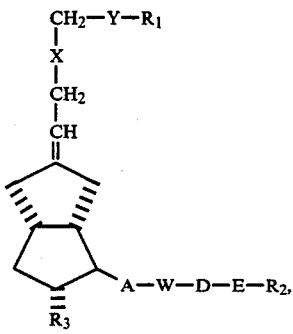

wherein $R_1$ is alkyl of 1-10 carbon atoms, cycloalkyl of 3-10 carbon atoms or an optionally substituted aryl group or aralkyl group of 6-10 carbon atoms, or a heterocyclic group, Y is a keto group or a free or functionally modified hydroxymethylene group, X is —$CH_2$— or an oxygen atom, A is —$CH_2$—$CH_2$—, trans—CH=CH— or —C≡C—, W is a free or functionally modified hydroxymethylene group or a free or functionally modified

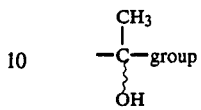

wherein the OH-group can be in the alpha- or beta-position,

D is

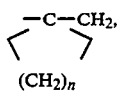

a straight-chain, saturated alkylene group of 1-10 carbon atoms, a branched, saturated or a straight-chain or branched, unsaturated alkylene group of 2-10 carbon atoms, all of which can optionally be substituted by 1-2 fluorine atoms, n is 1, 2 or 3, E is a direct bond, a —C≡C-group or a —$CR_4$=$CR_5$-group, wherein $R_4$ is hydrogen or alkyl of 1-5 carbon atoms and $R_5$ is hydrogen, halogen or alkyl of 1-5 carbon atoms, $R_2$ is alkyl of 1-10 carbon atoms, cycloalkyl of 3-10 carbon atoms or an optionally substituted aryl group of 6-10 carbon atoms or a heterocyclic group, and $R_3$ is a free or functionally modified hydroxy group.

DETAILED DISCUSSION OF THE INVENTION

The compounds of Formula I represent (5E)- as well as (5Z)-isomers. The position 5 is based on the carbacyclin nomenclature (see above).

Suitable alkyl groups $R_1$ and $R_2$ are straight- and branched-chain, saturated and unsaturated alkyl or alkenyl residues, preferably saturated, i.e., alkyl groups, of 1-10, especially 1-7 carbon atoms which can be substituted by optionally substituted aryl groups. Examples include methyl, ethyl, propyl, butyl, isobutyl, tert-butyl, pentyl, hexyl, heptyl, octyl, butenyl, isobutenyl, propenyl, pentenyl, hexenyl, benzyl and p-chlorobenzyl. Suitable substituents on the aryl substituents are those discussed below for $R_1$ aryl groups.

The cycloalkyl groups $R_1$ and $R_2$, can contain 3-10, preferably 3-6, carbon atoms in the ring. The rings can be substituted by alkyl groups of 1-4 carbon atoms. Examples include cyclopropyl, cyclobutyl, cyclopentyl, cyclohexyl, methyl-cyclohexyl and adamantyl.

Examples of substituted or unsubstituted aryl groups $R_1$ and $R_2$, include: phenyl, 1-naphthyl and 2-naphthyl which can each be substituted by 1-3 halogen atoms, a phenyl group, 1-3 alkyl groups of 1-4 carbon atoms each, or a chloromethyl, fluoromethyl, trifluoromethyl, carboxy, $C_1$-$C_4$-alkoxy, or hydroxy group. Preferred is subtitution in the 3- or 4-positions on the phenyl ring, for example by fluorine, chlorine, $C_1$-$C_4$-alkoxy or trifluoromethyl, or in the 4-position by hydroxy.

Suitable heterocyclic groups $R_1$ and $R_2$ include 5- and 6-membered heterocycles, preferably aromatic, containing at least one hetero atom, preferably nitrogen, oxygen or sulfur. Examples include 2-furyl, 2-thienyl, 2-pyridyl, 4-pyridyl, 3-furyl, 3-thienyl, and others.

The alkylene group D can be a straight-chain alkylene residue of 1–10 carbon atoms or a branched-chain, saturated or unsaturated alkylene residue of 2–10 carbon atoms, preferably of 1–5 carbon atoms and of 2–5 carbon atoms, respectively, all of which can be substituted, if desired, by fluorine atoms. Examples include: methylene, fluoromethylene, ethylene, 1,2-propylene, ethylethylene, trimethylene, tetramethylene, pentamethylene, 1-methyltetramethylene, 1-methyltrimethylene, etc.

The alkyl groups $R_4$ and $R_5$ are straight-chain or branched, saturated alkyl groups of 1–5 carbon atoms as recited above for $R_1$ and $R_2$. $R_5$ as halogen can be chlorine and bromine, preferably chlorine.

The functionally modified hydroxy groups in Y, W and $R_3$ include acyloxy, e.g., alkanoyloxy groups of 2–10 carbon atoms, benzoyloxy, tetrahydropyranyloxy, tetrahydrofuranyloxy, trimethylsilyloxy, tribenzylsilyloxy or dimethyl-tert-butylsilyloxy.

Thus, this invention relates to carbacyclins of the formula

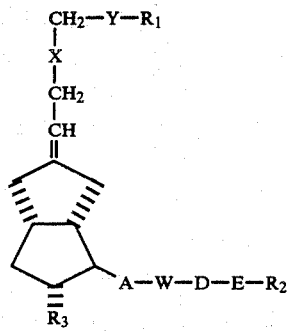

wherein $R_1$ is (a) $C_{1-10}$ alkyl, (b) $C_{1-10}$ alkyl substituted by $C_{6-10}$ aryl, or $C_{6-10}$ aryl substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy group, (c) $C_{2-10}$-alkenyl, (d) $C_{3-10}$ cycloalkyl, (e) $C_{3-10}$ cycloalkyl substituted by $C_{1-4}$ alkyl, (f) $C_{6-10}$ aryl, (g) $C_{6-10}$ aryl substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy group, or (h) an aromatic heterocycle of 5 or 6 ring atoms one of which is O, N or S, the remainder being carbon atoms, Y is —CO— or —CH(OR)—, X is —CH$_2$— or oxa, $R^3$ is OR, A is —CH$_2$—CH$_2$—, trans—CH=CH— or —C≡C—, W is —CH(OR)— or

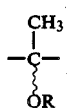

the OR-group can be in the alpha- or beta-position,

D is

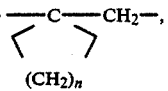

alkylene of 1–10 carbon atoms, or alkenylene of 2–10 carbon atoms, each of which can be substituted by fluorine, n is 1, 2 or 3, E is a direct bond, —C≡C— or —CR$_4$=CR$_5$—, wherein $R_4$ is hydrogen or alkyl of 1–5 carbon atoms and $R_5$ is hydrogen, halogen or alkyl of 1–5 carbon atoms, $R_2$ is (a) $C_{1-10}$ alkyl, (b) $C_{1-10}$ alkyl substituted by $C_{6-10}$ aryl, or $C_{6-10}$ aryl substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy group, (c) $C_{2-10}$-alkenyl, (d) $C_{3-10}$ cycloalkyl, (e) $C_{3-10}$ cycloalkyl substituted by $C_{1-4}$ alkyl, (f) $C_{6-10}$ aryl, (g) $C_{6-10}$ aryl substituted by 1–3 halogen atoms, a phenyl group, 1–3 $C_{1-4}$ alkyl groups or a chloromethyl, fluoromethyl, trifluoromethyl, carboxy, hydroxy or $C_{1-4}$ alkoxy group, or (h) an aromatic heterocycle of 5 or 6 ring atoms one of which is O, N or S, the remainder being carbon atoms, R is H, tetrahydropyranyl, tetrahydrofuranyl, alpha-ethoxyethyl, trimethylsilyl, dimethyl-tert-butylsilyl, tribenzylsilyl or an acyl group of a $C_{2-10}$-hydrocarbon carboxylic or sulfonic acid, and those wherein AWDER$_2$ is

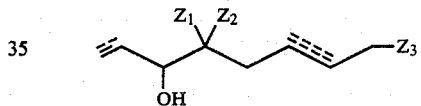

wherein ===== is a double or triple bond ======== is a single, double or triple bond, and each of $Z_1$, $Z_2$ and $Z_3$ independently is H or $C_{1-4}$-alkyl.

The invention furthermore relates to a process for the preparation of the carbacyclin derivatives of Formula I, characterized in that a compound of Formula II

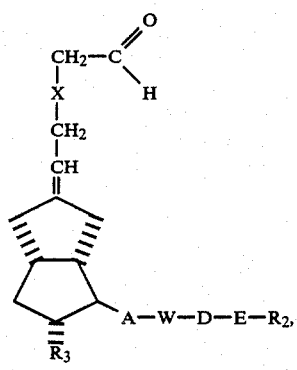

wherein $R_2$, $R_3$, X, A, W, D and E are as defined above and free hydroxy groups in W and $R_3$, if desired, are blocked intermediarily, is reacted with organometallic compounds of Formula III Me—R$_1$                  (III)

wherein
R₁ is as defined above and
Me is an alkali metal or a magnesium halide residue customary in Grignard reagents,
and, optionally, subsequently a resultant 1-hydroxy group is oxidized and/or blocked hydroxy groups are liberated and/or free hydroxy groups are esterified or etherified.

The reaction of the compounds of Formula II with the organometallic compound of Formula III can take place in an inert solvent or solvent mixture, e.g., diethyl ether, tetrahydrofuran, dioxane, toluene, preferably tetrahydrofuran or diethyl ether. The reaction is performed at temperatures of -100° C. to 60° C., preferably at −70° to 30° C.

The compounds of Formula III, required for this reaction, can be produced, for example, by reacting the corresponding halogen compound with an alkali or alkaline earth metal (e.g., magnesium) according to conventional methods.

The produced 1-hydroxy group is oxidized according to methods known to those skilled in the art. The oxidizing agent employed, for example, can be: pyridinium dichromate (Tetrahedron Letters, 1979 : 399), Jones reagent (J. Chem. Soc. 1953 : 2555) or platinum/oxygen (Adv. in Carbohydrate Chem. 17 : 169 [1962]) or Collins oxidation. The oxidation with pyridinium chromate is conducted at temperatures of 0° to 100° C., preferably 20°–40° C., in a solvent inert with respect to the oxidizing agent, e.g., dimethylformamide.

The oxidation with Jones reagent is conducted at temperatures of −40° to +40° C., preferably from 0° to 30° C., in acetone as the solvent.

The oxidation with platinum/oxygen is performed at temperatures of 0° C. to 60° C., preferably from 20° to 40° C., in a solvent inert with respect to the oxidizing agent, such as, for example, ethyl acetate.

The functional modification of the free OH-groups also takes place according to methods known to persons skilled in the art. For introduction of the ether blocking groups, for example, the reaction can be conducted with dihydropyran in methylene chloride or chloroform with the use of an acidic condensation agent, e.g., p-toluenesulfonic acid. The dihydropyran is used in excess, preferably in four to ten times the amount required theoretically. The reaction is normally completed at 0° C.–30° C. after 15–30 minutes.

The acyl blocking groups can be introduced by conventionally reacting a hydroxy-compound with a carboxylic acid derivative, e.g., an acid chloride, acid anhydride, etc.

The liberation of a functionally modified OH-group to obtain the compounds of general Formula I takes place by methods also known, per se. For example, ether blocking groups can be split off in an aqueous solution of an organic acid, such as, for example, acetic acid, propionic acid, etc., or in an aqueous solution of an inorganic acid, e.g., hydrochloric acid. In order to improve solubility, a water-miscible, inert organic solvent is suitably added. Suitable organic solvents include, for example, alcohols, such as methanol and ethanol, and ethers, such as dimethoxyethane, dioxane, and tetrahydrofuran. Tetrahydrofuran is preferably employed. The splitting-off step is conducted preferably at temperatures of between 20° and 80° C.

The silyl ether blocking groups can be split off, for example, with tetrabutylammonium fluoride. Examples of suitable solvents include tetrahydrofuran, diethyl ether, dioxane, methylene chloride, etc. The splitting-off step is preferably conduted at temperatures of 0° to 80° C.

The acyl groups can be saponified, for example, with alkali or alkaline earth carbonates or hydroxides in an alcohol or in the aqueous solution of an alcohol. Suitable alcohols include aliphatic alcohols, e.g., methanol, ethanol, butanol, etc., preferably methanol. Alkali carbonates and hydroxides than be mentioned are potassium and sodium salts, but the potassium salts are preferred. Suitable alkaline earth carbonates and hydroxides include, for example, calcium carbonate calcium hydroxide, and barium carbonate. The reaction can occur at −10° to 70° C., preferably at 25° C.

The compounds of Forumula II serving as the starting material can be prepared, for example, after first blocking any free hydroxy groups, by reducing a methyl ester of Formula IV

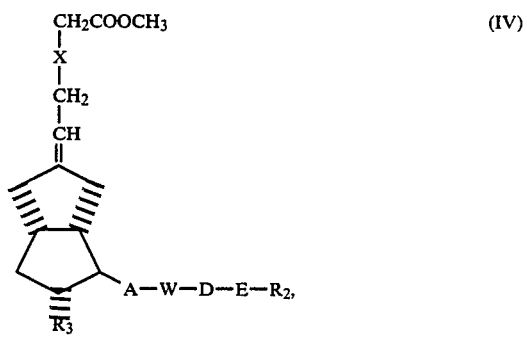

(IV)

wherein X, A, W, D, E, R₂ and R₃ are as defined above, with lithium aluminum hydride in diethyl ether and/or tetrahydrofuran, according to DOS No. 3,121,155, to form the primary alcohol of Formula V

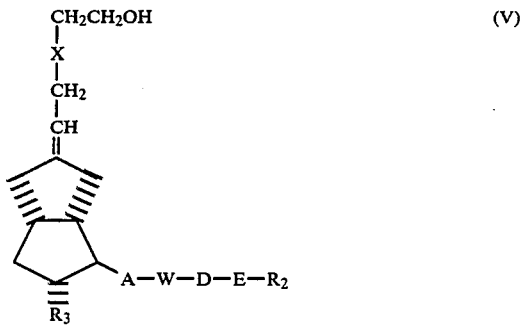

(V)

and subsequently oxidizing with Collins reagent or pyridine dichromate or pyridinium chlorochromate.

Another method for producing the compounds of Formula II resides in selective reduction of the ester of Formula IV with diisobutyl aluminum hydride at low temperatures, preferably −70° C., in inert solvents or solvent mixtures, such as, for example, toluene, tetrahydrofuran or methylene chloride.

The methyl esters of Formula IV are all known and/or readily preparable, from the free carboxylic acids disclosed, for example, in DOS Nos. 2,845,770; 3,048,906; 3,204,443; 3,209,702; 3,306,123; 3,306,125, or produced in analogous fashion, by esterification with diazomethane at 0° C. in methylene chloride. The blocking of free hydroxy groups in R₃ and W that may be necessary can take place, for example, by etherification with dihydropyran or by silylation.

The compounds of Formula I of this invention have cytoprotective activity. They are suitable as prophylactics and therapeutical agents for the treatment of cell damage. Consequently, the novel carbacyclin derivatives of Formula I constitute valuable pharmaceutically effective agents. As compared with $PGI_2$, they are distinguished by higher stability. The high specificity of effectiveness of the novel carbacyclins is demonstrated in a test on smooth-muscle organs, such as, for example, on guinea pig ileum or on isolated rabbit trachea where a substantially lower stimulation can be observed than in the administration of natural prostaglandins.

The novel carbacyclin analogs exhibit several of the properties typical for prostacyclins, such as, for example, myocardial cytoprotection without simultaneously lowering stroke volume and coronary blood flow, and gastrointestinal cytoprotection. They are suitable for the treatment of stroke, for the prophylaxis and therapy of coronary heart disease, prophylaxis and therapy of ischemic attacks of the CNS system, cytoprotection of gastric and intestinal mucosa, and cytoprotection in liver, kidney, and pancreas.

The carbacyclins of this invention can also be utilized in combination, for example, with beta-blockers, diuretics, phosphodiesterase inhibitors, calcium antagonists, nonsteroidal anti-inflammatory agents, leukotriene synthesis inhibitors, leukotriene antagonists, thromboxane synthesis inhibitors or thomboxane antagonists.

The dosage of the compounds is 1–1,500 µg/kg day when administered to human patients for any of the above uses analogously to the known agent Iloprost. The unit dosage in a pharmaceutically acceptable carrier is 0.01–100 mg. Sterile, injectable, aqueous or oily solutions are suitable for parenteral administration. Suitable for oral administration are, for example, tablets, dragees or capsules.

The invention accordingly also concerns medicinal agents based on the compounds of Formula I and conventional auxiliary agents and excipients, including cyclodextrin clathrates. The active compounds of this invention can be utilized in conjunction with the auxiliary agents known and customary in galenic pharmacy, for example, for the preparation of cytoprotective agents. Thus, the pharmacologically active compounds of this invention can be processed in accordance with conventional methods of galenic pharmacy to produce medicinal agents for administration to patients, e.g., mammals, including humans. Conventional excipients are pharmaceutically acceptable organic or inorganic carrier substances suitable for parenteral, enteral or topical application which do not deleteriously react with the active compounds. Suitable pharmaceutically aceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories, or capsules having talc and/or a carbohydrate carrier or binder or the like, the carrier preferably being lactose and/or corn starch and/or potato starch. A syrup, elixer or the like can be used wherein a sweetened vehicle is employed. Sustained release compositions can be formulated including those wherein the active compound is protected with differentially degradable coatings, e.g., by microencapsulation, multiple coatings, etc.

Dosages for a given host can be determined using conventional considerations, e.g., by customary comparison of the differential activities of the subject compound and of a known agent, e.g., $PGI_2$, by means of an appropriate, conventional pharmacological protocol.

The novel prostaglandin analogs of this invention are substantially more selective with regard to potency, as compared with known PG analogs in causing prostaglandin-like biological responses, and have a substantially longer duration of biological activity. Accordingly, each of these novel prostaglandin analogs is surprisingly and unexpectedly more useful than one of the corresponding conventional prostaglandins for at least one of the pharmacological purposes indicated above because it has a different and narrower spectrum of biological potency than the known prostaglandin, and therefore is more specific in its activity and causes smaller and fewer undesired side effects than when the prostaglandin is used for the same purpose. Moreover, because of its prolonged activity, fewer and smaller does of the novel prostaglandin analog are frequently effective in attaining the desired result.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the following examples, all temperatures are set forth uncorrected in degrees Celsius; unless otherwise indicated, all parts and percentages are by weight.

EXAMPLE 1

(5E)-(16RS)-2-Decarboxy-2-(1-hydroxyethyl)-16-methyl-18,18,19,19-tetradehydro-6a-carbaprostaglandin $I_2$ At $-70°$ C., 25 ml of a 1.6-molar ethereal methyllithium solution is added to a solution of 513 mg of (5E)-(16RS)-2-decarboxy-2-formyl-16-methyl-18,18,19,19-tetrahydro-6a-carbaprostaglandin $I_2$ 11,15-bis(tetrahydropyranylether) in 13 ml of diethyl ether and 13 ml of tetrahydrofuran, and the mixture is stirred for 4 hours at $0°$ C. Then it is poured on saturated ammonium chloride solution, extracted with ether, the organic phase is washed neutral with water, dried over magnesium sulfate and evaporated under vacuum. The residue is chromatographed with ether/hexane (1+1) on silica gel, thus obtaining 428 mg of (5E)-(16RS)-2-decarboxy-2-(1-hydroxyethyl)-16-methyl-18,18,19,19-tetrahydro-6a-carbaprostaglandin $I_2$ 11,15-bis(tetrahydropyranyl ether) as a colorless oil.

IR (CHCl$_3$): 3600, 3450, 2935, 2860, 1602, 1452, 971 cm$^{-1}$.

To split off the blocking groups, 428 mg of the above-prepared alcohol is agitated for 16 hours at 25° C. with 38 ml of a mixture of acetic acid/water/tetrahydrofuran (65/35/10), evaporated while adding toluene, and the residue chromatographed on silica gel with ethyl acetate, yielding 295 mg of the title compound as a colorless oil.

IR: 3600, 3400 (broad), 2925, 2860, 1602, 1450, 970 cm$^{-1}$.

The starting material for the above title compound is produced as follows:

1(a)

(5E)-(16RS)-2-Decarboxy-2-formyl-16-methyl-18,18,19,19-tetradehydro-6a-carbaprostaqlandin I$_2$ 11,15-Bis(tetrahydropyranyl ether)

At 0° C., an ethereal solution of diazomethane is added dropwise to a solution of 2 g of (5E)-(16RS)-16-methyl-18,18,19,19-tetradehydro-6a-carbaprostaglandin I$_2$ in 150 ml of methylene chloride until the mixture assumes a permanent yellow coloring. The mixture is stirred for 5 minutes and then evaporated under vacuum. The resultant methyl ester is dissolved in 50 ml of methylene chloride, cooled to 0° C., 1.8 g of dihydropyran and 20 mg of p-toluenesulfonic acid are added, and the mixture is agitated for 30 minutes at 0° C. Then the mixture is diluted with ether, shaken with dilute sodium bicarbonate solution, washed neutral with water, dried over magnesium sulfate and evaporated under vacuum. Chromatography of the residue on silica gel yields with hexane/ether (1+1) 2.25 g of the 11,15-bis-tetrahydropyranyl ether.

For reducing purposes, 2.25 g of the above-obtained tetrahydropyranyl ether is dissolved in 130 ml of toluene and, at −70° C., an approximately 1.2-molar solution of diisobutyl aluminum hydride in toluene is added dropwise thereto; the mixture is stirred for 30 minutes at −70° C.

Subsequently, in succession, 5 ml of isopropanol and 2.5 ml of water are added dropwise, the mixture is stirred for 2 hours at 20° C., filtered and evaporated under vacuum. The residue is chromatographed on silica gel with hexane/ether (3+2), thus obtaining 1.85 g of the title compound as a colorless oil.

IR: 2940, 2850, 2720, 1720, 1600, 1450, 971 cm$^{-1}$.

EXAMPLE 2

(5E)-(16RS)-2-Acetyl-2-decarboxy-16-methyl-18,18,19,19-tetradehydro-6a-carbaprostaglandin I$_2$ A solution of 244 mg of (5E)-(16RS)-2-decarboxy-2-(1-hydroxyethyl)-16-methyl-18,18,19,19-tetradehydro.6a-carbaprostaglandin I$_2$ 11,15-bis(tetrahydropyranyl ether) (from Example 1) in 7 ml of methylene chloride is added at 0° C. to a solution of 1 g of Collins reagent (chromic acid-pyridine complex) in 14 ml of methylene chloride and agitated for 15 minutes at 0° C. Then the mixture is combined with ether, filtered, the filtrate washed in succession with water, 5% sodium bicarbonate solution, 10% sulfuric acid and water, dried over magnesium sulfate and evaporated under vacuum.

To split off the blocking groups, the evaporation residue is stirred for 16 hours at 25° C. with 24 ml of acetic acid/water/tetrahydrofuran (65/35/10), evaporated under vacuum while adding toluene, and the residue is chromatographed on silica gel with ethyl acetate, yielding 125 mg of the title compound as a colorless oil.

IR: 3600, 3340 (broad), 2930, 1710, 1603, 1450, 1430, 1360, 970 cm$^{-1}$.

EXAMPLE 3

(5E)-(16RS)-2-Decarboxy-16,20-dimethyl-2-(1-hydroxyethyl)-18,18,19,19-tetradehydro-6a-carbaprostaglandin I$_2$ Analogously to Example 1, 590 mg of (5E)-(16RS)-2-decarboxy-16,20-dimethyl-2-formyl-18,18,19,19-tetradehydro-6a-carbaprostaglandin I$_2$ 11,15-bis(tetrahydropyranyl ether) yields 440 mg of (5E)-(16RS)-2-decarboxy-16,20-dimethyl-2-(1-hydroxyethyl)-18,18,19,19-tetradehydro-6a-carbaprostaglandin I$_2$ 11,15-bis(tetrahydropyranyl ether) as a colorless oil.

IR: 3600, 3440, 2935, 2860, 1602, 1453, 970 cm$^{-1}$.

After splitting off the blocking groups as in Example 1, 310 mg of the title compound is obtained as a colorless oil.

IR: 3600, 3410 (broad), 2927, 2861, 1602, 1451, 971 cm$^{-1}$.

The starting material for the above title compound is prepared as follows:

3(a)

(5E)-(16RS)-2-Decarboxy-16,20-dimethyl-2-formyl-18,18,19,19-tetradehydro-6 a-carbaprostaglandin I$_2$ 11,15-Bis(tetrahydropyranyl ether)

Analogously to Example 1(a), 2.5 g of (5E)-(16RS)-16,20-dimethyl-18,18,19,19-tetradehydro-6 a-carbaprostaglandin I$_2$ yields 2.1 g of the title compound as a colorless oil.

IR: 2940, 2852, 2721, 1720, 1602, 1450, 972 cm$^{-1}$.

EXAMPLE 4

(5E)-(16RS)-2-Acetyl-2-decarboxy-16,20-dimethyl-18,18,19,19-tetradehydro-6 a-carbaprostaglandin I$_2$ In analogy to Example 2, 320 mg of (5E)-(16RS)-2-decarboxy-16,20-dimethyl-2-(1-hydroxyethyl)-18,18,19,19-tetradehydro-6 a-carbaprostaglandin I$_2$ 11,15-bis(tetrahydro-pyranyl ether) yields 180mg of the title compound as a colorless oil.

IR: 3610, 3330 (broad), 2930, 1710, 1602, 1450, 1430, 971 cm$^{-1}$.

EXAMPLE 5

(5E)-2-Decarboxy-16,16-dimethyl-2-(1-hydroxyethyl)-18,18,,19,19-tetradehydro-6a-carbaprostaglandin I$_2$ In analogy to Example 1, 620 mg of (5E)-2-decarboxy-16,16 -dimethyl-2-formyl-18,18,19,19-tetradehydro-6a-carbaprostaglandin I$_2$ 11, 15-bis(tetrahydropyranyl ether) yields 465 mg of (5E)-2-decarboxy-16,16-dimethyl-2-(1-hydroxyethyl)-18,18,19,19-tetradehydro-6 a-carbaprostaglandin I$_2$ 11,15-bis(tetrahydropyranyl ether) as a colorless oil.

IR: 3600, 3430, 2935, 2860, 1601, 1453, 972 cm$^{-1}$.

After splitting off the blocking groups according to Example 1, 340 mg of the title compound is obtained as a colorless oil.

IR: 3600, 3400 (broad), 2930, 2860, 1601, 1450, 970 cm$^{-1}$.

The starting material for the above title compound is produced as follows:

5(a)

(5E)-2-Decarboxy-16,16-dimethyl-2-formyl-18,18,19,19-tetradehydro-6 a-carbaprostaglandin I$_2$ 11,15-Bis(tetrahydropyranyl ether)

Analogously to Example 1(a), 2.3 g of (5E)-16,16-dimethyl-18,18,19,19-tetradehydro-6a-carbaprostaglandin I$_2$ yields 1.9 g of the title compound as a colorless oil.

IR: 2940, 2860, 2720, 1718, 1601, 1450, 971 cm$^1$.

EXAMPLE 6

(5E)-2-Acetyl-2-decarboxy-16,16-dimethyl-18,18,19,19-tetradehydro-6a-carbaprostaglandin I$_2$ Analogously to Example 2, 250 mg of (5E)-2-decarboxy-16,16-dimethyl-2-(1-hydroxyethyl)-18,18,19,19-tetradehydro-6 a-carbaprostaglandin I$_2$ 11,15-bis(tetrahydropyranyl ether) yields 125 mg of the title compound as a colorless oil.

IR: 3600, 3320 (broad), 2932, 1710, 1601, 1450, 970 cm$^{-1}$.

EXAMPLE 7

(5E)-2-Decarboxy-2-(1-hydroxyethyl)-16,16,20-trimethyl-18,18,19,19-tetradehydro-6 a-carbaprostaglandin I$_2$ In analogy to Example 1, 580 mg of (5E)-2-decarboxy2-formyl-16,16,20-trimethyl-18,18,19,19 -tetradehydro-6a-carbaprostaglandin I$_2$ 11,15-bis(tetrahydropyranyl ether) yields 420 mg of (5E)-2-decarboxy-2-(1-hydroxyethyl)-16, 16,20-trimethyl-18,18,19,19-tetradehydro-6a-carbaprostaglandin I$_2$ 11,15-bis(tetrahydropyranyl ether) as a colorless oil.

IR: 3600, 3420, 2936, 2862, 1602, 973 cm$^{-1}$.

After splitting off the blocking groups as in Example 1, 290 mg of the title compound is produced as a colorless oil.

IR: 3600, 3420 (broad), 2930, 2860, 1602, 1452, 971 cm$^{-1}$.

The starting material for the above title compound is produced as follows:

7(a)

(5E)-2-Decarboxy-2-formyl-16,16,20-trimethyl-18,18,19,19 -tetradehydro-6a-carbaprostaglandin I$_2$ 11,15-Bis(tetrahydropyranyl ether)

Analogously to Example 1(a), 1.9 g of (5E)-16,16,20-trimethyl-18,18,19,19-tetradehydro-6a-carbaprostaglandin I$_2$ produces 1.54 g of the title compound as a colorless oil.

IR: 2942, 2861, 2721, 1718, 1602, 1452, 970 cm$^{-1}$.

EXAMPLE 8

(5E)-2-Acetyl-2-decarboxy-16,16,20-trimethyl-18,18,19,19-tetradehydro-6a-carbaprostaglandin I$_2$ Analogously to Example 2, 230 mg of (5E)-2-decarboxy-2-(1-hydroxyethyl)-16,16,20-trimethyl-18,18,19,19-tetradehydro-6a-carbaprostaglandin I$_2$ 11,15-bis(tetrahydropyranyl ether) yields 110 mg of the title compound as a colorless oil.

IR: 3600, 3310 (broad), 2930, 1710, 1602, 1451, 971 cm$^{-1}$.

EXAMPLE 9

(5E)-(16RS)-2-Decarboxy-2-(1-hydroxyethyl)-16-methyl-6 a-carbaprostaglandin I$_2$.

Analogously to Example 1, 0.9 g of (5E)-(16RS)-2decarboxy-2-formyl-16-methyl-6a-carbaprostaglandin I$_2$ 11,15-bis(tetrahydropyranyl ether) yields 0.7 g of (5E)-(16RS)-2 -decarboxy-2-(1-hydroxyethyl)-16-methyl-6a-carbaprostaglandin I$_2$ 11,15-bis(tetrahydropyranyl ether) as a colorless oil.

IR: 3605, 3400 (broad), 2935, 2860, 1600, 972 cm$^{-1}$.

After splitting off the blocking groups according to Example 1, 0.4 g of the titel compound is obtained as a colorless oil.

IR: 3610, 3400 (broad), 2935, 2860, 1600, 972 cm $^{-1}$.

The starting material for the above title compound is prepared as follows:

9(a)

(5E)-(16RS)-2-Decarboxy-2-formyl-16-methyl-6a-carbaprostaglandin I$_2$ 11,15-Bis(tetrahydropyranyl ether)

Analogously to Example 1(a), 3.9 g of (5E)-(16RS)-methyl-6a-carbaprostaglandin I$_2$ yields 3.1 g of the title compound as a colorless oil.

IR: 2940, 2860, 1718, 1600, 1451, 972 cm$^{-1}$.

EXAMPLE 10

(5E)-(16RS)-2-Acetyl-2-decarboxy-16-methyl-6a-carbaprostaglandin I$_2$

In analogy to Example 2, 400 mg of (5E)-(16RS)-2-decarboxy-2-(1-hydroxyethyl)-16-methyl-6 a-carbaprostaglandin I$_2$ 11,15-bis(tetrahydropyranyl ether) yields 230 mg of the title compound as a colorless oil.

IR: 3610, 3300 (broad), 2932, 1710, 1601, 1450, 970 cm$^{-1}$.

EXAMPLE 11

(5E)-2-Decarboxy-16,16-dimethyl-2-(1-hydroxyethyl)-6 a-carbaprostaglandin I$_2$

In analogy to Example 1, 0.5 g of (5E)-2-decarboxy-16,16-dimethyl-2-formyl-6a-carbaprostaglandin I$_2$ 11,15-bis(tetrahydropyranyl ether) yields 0.38 g of (5E)-2-decarboxy-16,16-dimethyl-2-(1-hydroxyethyl)-6a-carbaprostaglandin I$_2$ 11,15-bis(tetrahydropyranyl ether) as a colorless oil.

IR: 3600, 3410 (broad), 2936, 2862, 1602, 971 cm$^{-1}$.

After splitting off the blocking groups as disclosed in Example 1, 0.22 g of the title compound is obtained as a colorless oil.

IR: 3600, 3410 (broad), 2935, 2860, 1602, 971 cm$^{-1}$.

The starting material for the above title compound is produced as set out below:

11(a)

(5E)-2-Decarboxy-16,16-dimethyl-2-formyl-6a-carbaprostaglandin I$_2$ 11,15-Bis(tetrahydropyranyl ether)

Analogously to Example 1(a), 2.2 g of (5E)-16,16-dimethyl-6 a-carbaprostaglandin I2 produces 1.9 g of the title compound as a colorless oil.

IR: 2942, 2861, 1719, 1602, 1450, 971 cm$^{-1}$.

EXAMPLE 12

(5E)-2-Acetyl-2-decarboxy-16,16-dimethyl-6a-carbaprostaglandin I$_2$

In analogy to Example 2, 0.18 g of (5E)-2-decarboxy-16,16 -dimethyl-2-(1-hydroxyethyl)-6a-carbaprostaglandin I$_2$ 11,15-bis(tetrahydropyranyl ether) yields 0.1 g of the title compound as a colorless oil.

IR: 3600, 3310 (broad), 2933, 1712, 1602, 1451, 972 cm$^{-1}$.

EXAMPLE 13

(5E)-(16RS)-2-Decarboxy-13,14-didehydro-16,20-dimethyl-2-(1-hydroxyethyl)-18,18,19,19-tetradehydro-6a-carbaprostaglandin I$_2$ Analogously to Example 1, 410 mg of (5E)-(16RS)-2decarboxy-13,14-didehydro-16,20-dimethyl-2-formyl-18,18,19,19 -tetradehydro-6a-carbaprostaglandin I$_2$ 11,15-bis (tetrahydropyranyl ether) yields 340 mg of (5E)-(16RS)-2-decarboxy-13,14-didehydro-16,20-dimethyl-2-(1-hydroxyethyl)-18,18,19,19-tetradehydro-6a-carbaprostaglandin I$_2$ 11,15-bis(tetrahydropyranyl ether) as a colorless oil.

IR: 3600, 3420, 2936, 2860, 2224 cm$^{-1}$.

After splitting off the blocking groups according to Example 1, 270 mg of the title compound is obtained as an oil.

IR: 3605, 3400 (broad), 2930, 2860, 2224 cm$^{-1}$.

The starting material for the above title compound is prepared as follows:

13(a)

(5E)-(16RS)-2-Decarboxy-13,14-didehydro-16,20-dimethyl-2-formyl-18, 18,19,19-tetradehydro-6a-carbaprostaglandin I$_2$ 11,15-Bis(tetrahydropyranyl ether)

Analogously to Example 1(a), 1.1 g of (5E)-(16RS)-13,14-didehydro-16,20-dimethyl-18,18,19,19-tetradehydro-6a-carbaprostaglandin I$_2$ yields 0.8 g of the title compound as a colorless oil.

IR: 2940, 2852, 2722, 2224, 1720 cm$^{-1}$.

EXAMPLE 14

(5E)-(16RS)-2-Acetyl-2-decarboxy-13,14-didehydro-16, 20-dimethyl-18,18,19,19-tetradehydro-6a-carbaprostaglandin I$_2$ Analogously to Example 2, 300 mg of (5E)-(16RS)-2decarboxy-13,14-didehydro-16,20-dimethyl-2-(1-hydroxy-ethyl)-18,18,19,19-tetradehydro-6a-carbaprostaglandin I$_2$ 11,15-bis(tetrahydropyranyl ether) yields 175 mg of the title compound as a colorless oil.

IR: 3600, 3320 (broad), 2930, 2224, 1710 cm$^{-1}$.

EXAMPLE 15

(5E)-(16S)-2-Decarboxy-13,14-didehydro-16,20-dimethyl-2 -(1-hydroxyethyl)-3-oxa-18,18,19,19-tetradehydro-6 a-carbaprostaglandin I$_2$ Analogously to Example 1, 360 mg of (5E)-(16S)-2-decarboxy-13,14-didehydro-16,20 -dimethyl-2-formyl-3-oxa-18,18,19,19-tetradehydro-6a-carbaprostaglandin I$_2$ 11,15-bis (tetrahydropyranyl ether) produces 270 mg of (5E)-(16S)-2 -decarboxy-13,14-didehydro-16,20-dimethyl-2-(1-hydroxyethyl)-3 -oxa-18,18,19,19-tetradehydro-6a-carbaprostaglandin I$_2$ 11,15-bis(tetrahydropyranyl ether) as a colorless oil.

IR: 3610, 3300 (broad), 2932, 2222 cm$^{-1}$.

After splitting off the blocking groups according to Example 1, 180 mg of the title compound is produced as a colorless oil.

IR: 3600, 3300 (broad), 2932, 2863, 2222 cm$^{-1}$.

The starting material for the above title compound is prepared as follows:

15(a)

(5E)-(16S)-2-Decarboxy-13,14-didehydro-16,20-dimethyl-2-formyl-3-oxa-18,18,19,19-tetradehydro-6a-carbaprostaglandin I$_2$ 11,15-Bis(tetrahydropyranyl ether)

In analogy to Example 1(a), 0.8 g of (5E)-(16S)-13,14-didehydro-16,20-dimethyl-3-oxa-18,18,19,19-tetradehydro-6 a-carbaprostaglandin I$_2$ yields 0.6 g of the title compound as a colorless oil.

IR: 2937, 2853, 2727, 2222, 1719 cm$^{-1}$.

EXAMPLE 16

(5E)-(16S)-2-Acetyl-2-decarboxy-13,14-didehydro-16,20 -dimethyl-3-oxa-18,18,19,19-tetradehydydro-6a-carbaprostaglandin I$_2$ In analogy to Example 2, 180 mg of (5E)-(16S)-2-decarboxy-13, 14-didehydro-16,20-dimethyl-2-(1-hydroxyethyl)-3-oxa-18,18,19,19-tetradehydro-6a-carbaprostaglandin I$_2$ 11,15-bis(tetrahydropyranyl ether) yields 85 mg of the title compound as a colorless oil.

IR: 3605, 3320 (broad), 2932, 2222, 1713 cm$^{-1}$.

EXAMPLE 17

(5E)-(16RS)-2-Decarboxy-2-(1-hydroxypentyl)-16-methyl-18,18,19,19-tetradehydro-6a-carbaprostaglandin I$_2$ At −70° C., 2.2 ml of a 1.6-molar butyllithium solution in hexane is introduced into a solution of 450 mg of (5E)-(16RS)-2-decarboxy-2-formyl-16-methyl-18,18,19,19-tetradehydro-6a-carbaprostaglandin I$_2$ 11,15-bis(tetrahydropyranyl ether) in 10 ml of diethyl ether and 10 ml of tetrahydrofuran; the mixture is stirred for 5 hours at 0° C. Then the mixture is poured on saturated ammonium chloride solution, extracted with ether, the organic phase is washed neutral with water, dried over magnesium sulfate and evaporated under vacuum. The residue is chromatographed with hexane/ether (6+4) on silica gel, thus obtaining 312 mg of (5E)-(16RS)-2-decarboxy-2-(1-hydroxypentyl)-16-methyl-18, 18,19,19-tetradehydro-6a-carbaprostaglandin I$_2$ 11,15-bis(tetrahydropyranyl ether) as a colorless oil.

IR: 3610, 3450 (broad), 2940, 2860, 1602, 1452, 972 cm$^{-1}$.

To split off the blocking groups, 312 mg of the above-produced alcohol is agitated for 16 hours at 25° C. with 28 ml of a mixture of acetic acid/water/tetrahydrofuran (65/35/10). The mixture is evaporated under vacuum while adding toluene and the residue chromatographed on silica gel with ethyl acetate, yielding 190 mg of the title compound as a colorless oil.

IR: 3600, 3400 (broad), 2935, 2860, 1601, 972 cm$^{-1}$.

EXAMPLE 18

(5E)-(16RS)-2-Decarboxy-16-methyl-2-valeryl-18, 18,19,19-tetradehydro-6a-carbaprostaglandin I$_2$ At 0° C., a solution of 235 mg of (5E)-(16RS)-2-decarboxy-2 -(1-hydroxypentyl)-16-methyl-18,18,19,19-tetradehydro-6a-carbaprostaglandin I$_2$ 11,15-bis(tetrahydropyranyl ether) (from Example 17) is added to a solution of 1 g of Collins reagent (chromic acid-pyridine complex) in 14 ml of methylene chloride, and the mixture is agitated for 20 minutes at 0° C. Then the mixture is combined with ether, filtered, the filtrate shaken in succession with water, 5% sodium bicarbonate solution, 10% sulfuric acid and water, dried over magnesium sulfate and evaporated under vacuum. To split off the blocking groups, the evaporation residue is stirred for 16 hours at 25° C. with 20 ml of acetic acid/water/tetrahydrofuran (65/35/10), evaporated under vacuum while adding toluene, and the residue is chromatographed on silica gel with ethyl acetate, yielding 110 mg of the title compound as a colorless oil.

IR: 3600, 2940, 2870, 1710, 970 cm$^{-1}$.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A carbacyclin of the formula

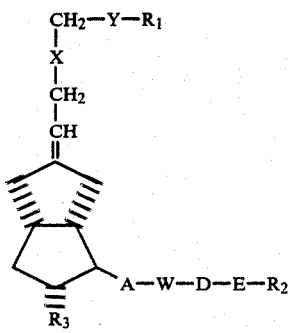

wherein $R_1$ is (a) $C_{1-10}$ alkyl, (b) $C_{1-10}$ alkyl substituted by $C_{6-10}$ aryl, or $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group, (c) $C_{2-10}$-alkenyl, (d) $C_{3-10}$ cycloalkyl, (e) $C_{3-10}$ cycloalkyl substituted by $C_{1-4}$ alkyl, (f) $C_{6-10}$ aryl, (g) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group, or (h) an aromatic heterocycle of 5 or 6 ring atoms one of which is O, N or S, the remainder being carbon atoms, Y is —CO—, X is —CH$_2$— or oxa, A is —CH$_2$—CH$_2$—, trans—CH=CH— or —C≡C—, W is —CH(OR)— or

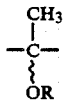

wherein in the OR-group can be in the alpha- or beta-position, is

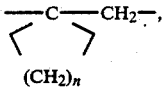

alkylene of 1-10 carbon atoms, alkenylene of 2-10 carbon atoms, each of which can be substituted by 1-2 fluorine, n is 1, 2 or 3, E is —C≡C—

$R_2$ is (a) $C_{1-10}$ alkyl, (b) $C_{1-10}$ alkyl substituted by $C_{6-10}$ aryl, or $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group, (c) $C_{2-10}$-alkenyl, (d) $C_{3-10}$ cycloalkyl, (e) $C_{3-10}$ cycloalkyl substituted by $C_{1-4}$ alkyl, (f) $C_{6-10}$ aryl, (g) $C_{6-10}$ aryl substituted by 1-3 halogen atoms, a phenyl group, 1-3 $C_{1-4}$ alkyl groups or a chloromethyl, fluoromethyl, trifluoromethyl, carboxy, hydroxy or $C_{1-4}$ alkoxy group, or (h) an aromatic heterocycle of 5 or 6 ring atoms one of which is O, N or S, the remainder being carbon atoms, and is H tetrahydropyranyl, tetrahydrofuranyl, alphaethoxyethyl, trimethylsilyl, dimethyl-tert-butylsilyl, tribenzylsilyl or an acyl group of a $C_{2-10}$-hydrocarbon carboxylic or sulfonic acid.

2. A compound of claim 1, wherein YR1 is —CO—CH$_3$.

3. A compound of claim 1, wherein X is —CH$_2$—.

4. A compound of claim 1, wherein AWDER$_2$ is

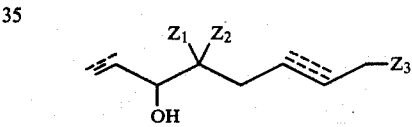

wherein ═══ is a double or triple bond ═══ is a triple bond, and each of $Z_1$, $Z_2$ and $Z_3$ independently is H or $C_{1-4}$-alkyl.

5. A compound of claim 4, wherein ═══ is a triple bond, each of $Z_1$, $Z_2$, is H or CH$_3$, and ═══ is a double bond.

6. (5E)-(16RS)-2-Acetyl-2-decarboxy-16-methyl-18,18,19,19-tetradehydro-6a-carbaprostaglandin I$_2$, a compound of claim 1.

7. (5E)-(16RS)-2-Acetyl-2-decarboxy-16,20-dimethyl-18,18,19,19-tetradehydro-6a-carbaprostaglandin I$_2$, a compound of claim 1.

8. (5E)2-Acetyl-2-decarboxy-16,16-dimethyl-18,18-19,19 -tetradehydro-6a-carbaprostaglandin I$_2$, a compound of claim 1.

9. (5E)-2-Acetul-2-decarboxy-16,16,20-trimethyl-18,18,19,19 - tetradehydro-6a-carbaprostaglandin I$_2$, a compound of claim 1.

10. (5E)-(16RS)-2-Acetyl-2-decarboxy-13,14-didehydro-16, 20-dimethyl-18, 18, 19, 19-tetradehydro-6a-carbaprostaglandin I$_2$, a compound of claim 1.

11. (5E)-(16S)-2-Acetyl-2-decarboxy-13,14-didehydro-16, 20-dimethyl-3-oxa-18,18,19,19-tetradehydro-6a-carbaprostaglandin I$_2$, a compound of claim 1.

12. (5E)-(16RS)-2-Decarboxy-16-methyl-2-valeryl-18, 18, 19, 19-tetradehydro-6a-carbaprostaglandin I$_2$, a compound of claim 1.

13. A pharmaceutical composition comprising a cytoprotective effective amount of a compound of claim 1 and a pharmaceutically acceptable carrier.

14. A method of achieving a cytoprotective effect in a patient comprising administering a cytoprotective amount of a compound of claim 1 to the patient.

15. A method of claim 1, wherein the cytoprotective effect is achieved with respect to the stomach, intestine, heart, kidneys, liver or pancreas.

16. A carbacyclin of the formula

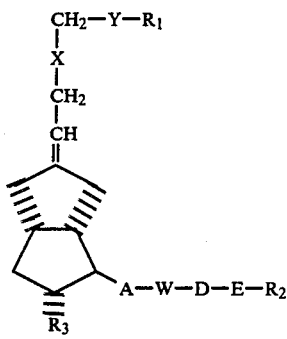

wherein
$R_1$ is (a) $C_{1-10}$ alkyl substituted by $C_{6-10}$ aryl, or $C_{6-10}$ aryl substituted by 1–3 halogen atoms, a phenyl group, 1–3 $C_{1-4}$ alkyl groups or a chloromethyl, fluromethyl, trifluoromethyl, carboxy, hydroxy or $C_{1-4}$ alkoxy group, (b) $C_{2-10}$-alkenyl, (c) $C_{3-10}$ cycloalkyl, (d) $C_{3-10}$ cycloalkyl substituted by $C_{1-4}$ alkyl, (e) $C_{6-1}$-aryl, (f) $C_{6-10}$ aryl substituted by 1–3 halogen atoms, a phenyl group, 1–3 $C_{1-4}$ alkyl groups or a chloromethyl, fluoromethyl, trifluoromenthyl, carboxy, hydroxy or $C_{1-4}$ alkoxy group, or (g) an aromatic heterocycle of 5 or 6 ring atoms one of which is O, N or S, the remainder being carbon atoms,
Y is —CO— or —CH(OR)—,
X is —CH$_2$— or oxa,
$R^3$ is OR,
A is —CH$_2$—CH$_2$—, trans—CH=CH— or —C≡C—,
W is —CH(OR)— or

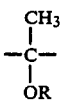

wherein the OR-group can be in the alpha- or beta-position,
is

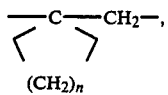

alkylene of 1–10 carbon atoms, alkenylene of 2–10 carbon atoms, each of which can be substituted by 1-fluroine,
n is 1, 2 or 3,
E is a direct bond, —C≡C— or —CR$_4$=CR$_5$—, wherein R$_4$ is hydrogen or alkyl of 1–5 carbon atoms and R$_5$ is hydrogen, halogen or alkyl of 1–5 carbon atoms,
$R_2$ is (a) $C_{1-10}$ alkyl, (b) $C_{1-10}$ alkyl substituted by $C_{6-10}$ aryl, or $C_{6-10}$ aryl substituted by 1–3 halogen atoms, a phenyl group, 1–3 $C_{1-4}$ alkyl groups or a chloromethyl, fluromethyl, trifluromethyl, carboxy, hydroxy or $C_{1-4}$ alkoxy group, (c) $C_{2-10}$-alkenyl, (d) $C_{3-10}$ cycloalkyl, (e) $C_{3-10}$ cycloalkyl substituted by $C_{1-4}$ alkyl, (f) $C_{6-10}$ aryl, (g) $C_{6-10}$ aryl substituted by 1–3 halogen atoms, a phenyl group 1–3 $C_{1-4}$ alkyl groups or a chloromethyl, fluoromethyl, trifluoromethyl, carboxy, hydroxy or $C_{1-4}$ alkoxy group, or (h) an aromatic heterocycle of 5 or 6 ring atoms one of which is O, N or S, the remainder being carbon atoms, and
R is H, tetrahydropyranyl, tetrahydrofuranyl, alphaethoxyethyl, trimethylsilyl, dimethyl-tert-butylsilyl, tribenzylsilyl or an acyl group of a $C_{2-10}$ -hydrocarbon carboxylic or sulfonic acid.

* * * * *

UNITED STATES PATENT AND TRADEMARK OFFICE
CERTIFICATE OF CORRECTION

PATENT NO. : 4,721,729

DATED : January 26, 1988

INVENTOR(S) : Werner Skuballa et al

It is certified that error appears in the above-identified patent and that said Letters Patent is hereby corrected as shown below:

Col. 15, Claim 1, Line 68:

should read: --D is--

Col. 16, Claim 1, Line 26:

should read: --R is H, tetrahydropyranyl, tetrahydrofuranyl, alphaethox- --

Col. 16 Claim 9, Line 56:

should read: --(5E)-2-Acetyl-2-decarboxy-16,16,20-trimethyl- --

Col. 18, Claim 16, Line 10:

should read: --D is--

Col. 18, Claim 16, Line 19:

should read: --1-2 fluorine,--

UNITED STATES PATENT AND TRADEMARK OFFICE
CERTIFICATE OF CORRECTION

PATENT NO. : 4,721,729

DATED : January 26, 1988

INVENTOR(S) : Werner Skuballa et al.

It is certified that error appears in the above-identified patent and that said Letters Patent is hereby corrected as shown below:

Col. 18, Claim 16, Line 21:

should read: --E is a direct bond, —C≡C— or —$CR_4$=$CR_5$—,--

Signed and Sealed this

Twenty-first Day of March, 1989

Attest:

DONALD J. QUIGG

Attesting Officer

Commissioner of Patents and Trademarks